United States Patent [19]

Siegel et al.

[11] Patent Number: 4,808,606
[45] Date of Patent: Feb. 28, 1989

[54] ALKENYLAZOLES, A PROCESS FOR THEIR PREPARATION AND THEIR USE

[75] Inventors: Herbert Siegel, Hofheim am Taunus; Wolfgang Raether, Dreieich; Walter Dittmar, Hofheim am Taunus, all of Fed. Rep. of Germany

[73] Assignee: Hoechst Aktiengesellschaft, Fed. Rep. of Germany

[21] Appl. No.: 909,697

[22] Filed: Sep. 22, 1986

[30] Foreign Application Priority Data

Sep. 23, 1985 [DE] Fed. Rep. of Germany ....... 3533823

[51] Int. Cl.$^4$ .................. A01N 43/653; A01N 43/50; C07D 249/08; C07D 233/60
[52] U.S. Cl. .................................... 514/383; 514/184; 514/399; 548/101; 548/262; 548/341
[58] Field of Search ............... 548/341, 101, 262; 514/399, 184, 383; 568/734, 821

[56] References Cited

U.S. PATENT DOCUMENTS

| | | | |
|---|---|---|---|
| 4,235,620 | 11/1980 | Lewis et al. | 71/92 |
| 4,315,764 | 2/1982 | Reiser et al. | 514/383 |
| 4,521,429 | 6/1985 | Meyer et al. | 548/262 |
| 4,670,454 | 6/1987 | Janssen et al. | 514/383 |

FOREIGN PATENT DOCUMENTS

| | | | |
|---|---|---|---|
| 0057365 | 10/1982 | European Pat. Off. | 548/262 |
| EPA-121081 | 10/1984 | European Pat. Off. | 548/262 |
| 0153657 | 9/1985 | European Pat. Off. | 548/262 |
| 2738640 | 3/1978 | Fed. Rep. of Germany | 548/262 |
| 2652313 | 8/1979 | Fed. Rep. of Germany | 548/268 |

OTHER PUBLICATIONS

Chemical Abstracts, vol. 94, No. 15, 121405k.
Chemical Abstracts, vol. 101, No. 7, 54998d.

Primary Examiner—Glennon H. Hollrah
Assistant Examiner—Patricia L. Morris
Attorney, Agent, or Firm—Finnegan, Henderson Farabow, Garrett & Dunner

[57] ABSTRACT

Alkenylazoles of formula I a/b

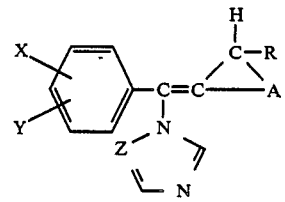

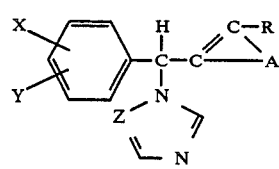

in which X/Y is H, alkyl, phenyl, Hal, alkoxy or alkylthio; Z is CH or N; R is alkyl or a bridged $(CH_2)_m$ chain; and A is alkylene or a bridged alkylene chain; and the salts of these alkenylazoles are antimycotic agents or fungicides. They are obtained by elimination of water from the compounds II

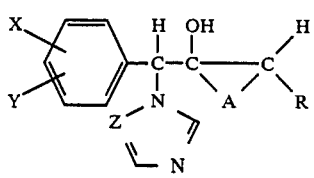

4 Claims, No Drawings

ALKENYLAZOLES, A PROCESS FOR THEIR PREPARATION AND THEIR USE

The invention relates to alkenylazoles, a process for their preparation and their use as antimycotic agents and fungicides.

It is known from European Published Application No. 57,365 and German Offenlegungsschrift No. 2,652,313 that alkenylazoles are suitable for combating fungi in humans, animals and plants. The effectiveness of these compounds is, however, not satisfactory, particularly at low concentrations.

The invention therefore relates to alkenylazoles of the general formula Ia/Ib

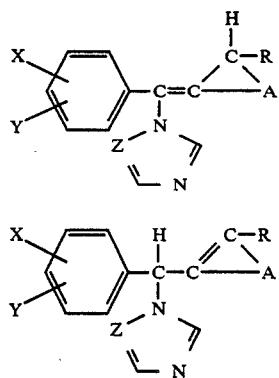

in which

X and Y are identical or different and denote H, $(C_1-C_4)$-alkyl, phenyl, F, Cl, Br, $(C_1-C_4)$-alkoxy or $(C_1-C_4)$-alkylthio, Z denotes CH or N, R denotes H or $(C_1-C_4)$-alkyl or, if A is a bridged $(CH_2)_m$ chain having m=4 and 3 bridge carbon atoms, denotes a methylene group attached to the middle bridge carbon atom, A is a $(CH_2)_n$ chain in which n=1-10 and which is unsubstituted or substituted by $(C_1-C_4)$-alkyl and phenyl, or A denotes a bridged $(CH_2)_m$ chain having m=3 or 4 and 1-5 bridge carbon atoms, and to their salts with acids and their stereoisomers. The two formulae Ia and Ib have either an exocyclic or an endocyclic C=C double bond.

Preferred compounds of the formula Ia/Ib are those in which X and Y are hydrogen, fluorine, chlorine or phenyl, R is H or $CH_2$ and A denotes a $(CH_2)_m$ chain in which n=3-5 or a briged $(CH_2)_m$ chain having m=3 or 4 and 1-5 bridge carbon atoms, it being necessary for at least one of these characteristics to be fulfilled. The preparation of the compounds, according to the invention, of the formula Ia/Ib is effected by eliminating water from carbinols of the formula II

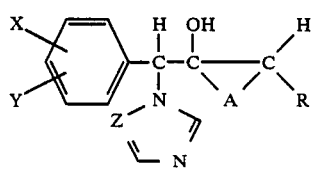

in which X, Y, Z, R and A have the meaning indicated for formula I.

The elimination of water from compounds of the formula II can, in principle be effected by methods described in the literature. Normally, the reaction is carried out in the liquid phase using acid dehydrating agents at temperatures between 0° and 150° C., preferably at 25°–100° C. Suitable acid dehydrating agents are inorganic and organic proton acids, such as sulfuric acid, acetic acid or p-toluenesulfonic acid, and anhydrides and acid chlorides thereof, acid salts, such as $KHSO_4$, or Lewis acids, such as, for example, boron fluoride or zinc chloride; it is preferable, however, to use a proton acid, such as sulfuric acid. The dehydrating agent can act at the same time as the solvent, but it is also possible to use inert other solvents, such as tetrahydrofuran or toluene, as against the dehydrating agent. Working up is effected by neutralization with aqueous alkali solution, the reaction product either being precipitated direct or being extracted with a solvent. The products are purified either by recrystallization or chromatography over silica gel.

The carbinols of the general formula II which are used as the precursor can be obtained by two routes, as described in the parallel German Patent Application No. P 3,533,824.5 (HOE 85/F 202).

In the first method, one or two equivalents of a strong base are added, for example in an aprotic polar solvent at a temperature between 25° and −100° C., to a benzylazole of the general formula III

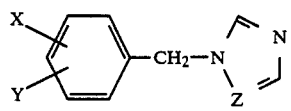

in which X, Y and Z have the meaning indicated for formula I, a carbonyl compound of the general formula IV

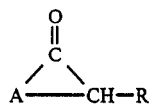

in which A and R have the meaning indicated for formula I, is added to the resulting carbanion, and the carbinol of the general formula II is finally obtained after the addition of a proton acid.

Suitable strong bases are, in particular, alkali metal hydrides, such as sodium hydride, or alkaline earth and alkali metal alkyls, such as, for example, butyllithium, or metalated amines, such as, for example, lithium diisopropylamide. The use of two equivalents of a strong base is necessary, for example, in the case of benzyltriazole derivatives, otherwise products which are hydroxyalkylated on the triazole ring are obtained. The reaction can be carried out in the solvents customary for organometallic reactions, such as dimethylformamide, dimethyl sulfoxide, dimethoxy ethane, diethyl ether or, preferably, tetrahydrofuran. Additionally, it is also possible to use solvent additives, such as N,N,N',N'-tetramethylethylenediamine or hexamethylphosphoric acid triamide. The reaction with the strong base and the carbonyl compound of the formula II can be carried out at temperatures between room temperature and 100° C., but takes place preferably in the range between −30° C. and −80° C. The compounds of the formula II are isolated in the manner known and customary for organometallic reactions. Purification of the compounds of the formula II is carried out as a rule by recrystallization from an organic solvent, such as, for example, hexane, cyclohexane, ethanol or ethyl acetate, or by column chromatography over silica gel.

The N-benzylazoles of the formula III which are used are obtained in accordance with known methods by alkylating imidazole or triazole with benzyl halides.

In the second method, the starting materials are oxiranes of the general formula V

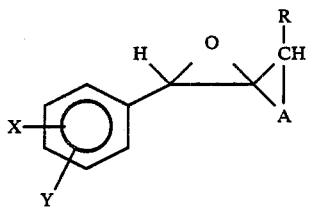

in which X, Y, R and A have the meaning indicated for formula I. The reaction leading to carbinols of the formula II is carried out by opening the epoxide of the formula V by means of an azole or sodium salt thereof at a temperature between 0° and 80° C., preferably in the range between 0° and 50° C., in a polar solvent. Oxiranes of the formula V are obtained by methods known from the literature. This is effected by first preparing the parent olefin and oxidizing the latter with a per-acid.

Acid addition salts can be prepared from the azole derivatives of the general formula I. Any acids which form physiologically acceptable salts are suitable for this purpose. These include not only inorganic acids, such as hydrochloric acid, nitric acid and sulfuric acid, but also monofunctional and bifunctional organic acids, in particular carboxylic acids, such as acetic acid, succinic acid or tartaric acid, or organic sulfonic acids, such as p-toluenesulfonic acid, benzenesulfonic acid and the like.

The new compounds of the general formula (I) and their acid addition salts are valuable drugs. In particular, they have an antimicrobial action and are suitable for the prophylaxis and treatment of fungal infections in humans and in various species of mammals.

The new compounds have a very good in vitro action against skin fungi, such as, for example, Trichophyton mentagrophytes, Microsporum canis and Epidermophyton floccosum; against mold fungi, such as, for example Aspergillus niger, or against yeasts, such as, for example, Candida albicans, C. tropicalis, Torulopsis glabrata and Trichosporon cutaneum, or against protozoa, such as Trichomonas vaginalis or T. fetus, or against Gram-positive and Gram-negative bacteria.

When administered orally or parenterally, the compounds also possess a good in vivo systemic effect, for example against Candida albicans, for example in experimental renal candidiasis of mice. There is also a very good effect against various pathogens of skin mycoses (for example 4 Trichophyton mentagrophytes) on guinea pigs after oral, parenteral or local administration.

The following are examples of suitable use forms of the compound according to the invention: tablets or capsules, suspensions, solutions, jellies, creams or ointments and also aerosols in the form of sprays.

The concentration to be used for solutions, jellies, creams or ointments and also aerosols in the form of spray is generally between 0.1 and 20, preferably 0.5 and 5, percent by weight.

Oral administration is effected in pharmaceutically customary formulations, for example in the form of tablets or capsules containing, per daily dose, 20-500 mg, preferably 50 to 300 mg, of the active compound, mixed with a customary excipient and/or constituents.

Suspensions, solutions, jellied, creams, ointments or suppositories can, for example, be used for local application.

Suitable suspensions or solutions, administered in a concentration between 0.1 and 5 percent by weight, are suitable for parenteral administration.

The compounds, according to the invention, of the formula I are distinguished by an excellent fungicidal action. It is possible to combat successfully, in a curative manner, fungal pathogens which have already penetrated into plant tissue. This is particularly important and advantageous in the case of fungal diseases which an no clonger be combated effectively by means of the otherwise customary fungicides after infection has set in. The spectrum of action of the claimed compounds covers a large number of different phytopathogenic fungi, such as, for example, Piricularia oryzae or Pellicularia sasakii, various species of rust and, in particular, Venturia inaequalis, species of Cercospora and powdery mildew fungi in the cultivation of fruit, vegetables, cereals and ornamental plants.

The compounds of the formula I are also suitable for use in industrial fields, for example as timber preservatives, as preservatives in paints and in cooling lubricants for metal machining or as preservatives in drilling and cutting oils.

The agents can be used in the customary formulations as wettable powders, emulsifiable concentrates, sprayable solutions, dusting agents, dressing agents, dispersions, granules or microgranules.

Wettable powders are preparations which are uniformly dispersible in water and which, in addition to the active compound and besides, if appropriate, a diluent or inert substance, also contain wetting agents, for example polyoxethylated alkyl phenols, polyoxethylated fatty alcohols, alkylsulfonates or alkylphenylsulfonates, and dispersing agents, for example sodium ligninsulfonate, sodium 2,2'-dinaphthylmethane-6,6'-disulfonate or sodium oleoylmethyl tauride. The preparation thereof is effected in a customary manner, for example by grinding and mixing the components.

Emulsifiable concentrates can be prepared, for example, by dissolving the active compound in an inert organic solvent, for example butanol, cyclohexanone, dimethylformamide, xylene or fairly high-boiling aromatic compounds or hydrocarbons, with the addition of one or more emulsifiers. In the case of liquid active compounds, the solventcomponent can also be wholly or partly dispensed with. The following are examples of emulsifiers which can be used:

Calcium alkylarylsulfonates, such as Ca dodecylbenzenesulfonate, or nonionic emulsifiers, such as fatty acid polyglycol esters, alkylaryl polyglycol ethers, fatty alcohol polyglycol ethers, propylene oxide/ethylene oxide condensation products, fatty alcohol/propylene oxide/ethylene oxide condensation products, alkyl polyglycol ethers, sorbitan fatty acid esters, polyoxethylenesorbitan fatty acid esters or polyoxethylenesorbitol esters.

Dusting agents can be obtained by grinding the active compound with finely divided solids, for example talc, natural clays, such as caolin, bentonite or pyrophyllite, or diatomaceous earth.

Granules can be prepared either by atomizing the active compound onto adsorpbent, granulated inert material or by applying concentrations of active compound by means of binders, for example polyvinyl alcohol, sodium polyacrylate or mineral oils, to the surface of carriers, such as sand or caolinite, or granulated inert material. Suitable active compounds can also be granulated—if desired as a mixture with fertilizers—in the manner customary for the preparation of fertilizer granules.

In wettable powders, the concentration of active compound is, for example about 10 to 90% by weight; the remainder up to 100% by weight consists of customary formulation ingredients. In the case of emulsifiable concentrates, the concentration of active compound can be about 10 to 80% by weight.

Formulations in the form of dust in most cases contain 5 to 20% by weight of active compound, while sprayable solutions contain about 2 to 20% by weight. In the case of granules, the active compound content depends in part on whether the active compound is present in a liquid or solid form and on the granulating auxiliaries, fillers and the like which are used.

In addition, the said formulations of active compounds contain, where appropriate, the tackifiers, wetting agents, dispersing agents, emulsifiers, penetration agents, solvents, fillers or carriers which are customary in a particular case.

For application, the concentrates, present in a commercial form, are, if appropriate, diluted in a customary manner, for example by means of water in the case of wettable powders, emulsifiable concentrates and dispersions and in part also in the case of microgranules. Formulations in the form of dust and granules and also sprayable solutions are usually not further diluted with other inert substances before use.

Mixtures or mixed formulations with other active compounds, such as, for example, insecticides, acaricides, herbicides, fertilizers, growth regulators or fungicides, are also possible in certain cases. Particularly in the case of mixtures with fungicides, synergistic increases in action are also achieved in some cases.

The following examples illustrate the preparation of the compounds according to the invention.

EXAMPLE 1

(Compound 1)

1-Imidazolyl-4-chlorophenyl-2-bicyclo[2.2.1]heptylidenemethane.

8.0 g (26.4 mmol) of 1-imidazolyl-(4-chlorophenyl)-(2-hydroxy-2-bicyclo[2.2.1]heptyl)-methane were dissolved in a mixture of 48 ml of glacial acetic acid and 12 ml of concentrated sulfuric acid, and the mixture was heated at 100° C. for 2 hours. The reaction mixture was then cooled and added, with cooling, to 200 ml of 25% sodium hydroxide solution.

The mixture was extracted with methylene chloride, the organic phase was dried and concentrated and 6.5 g of crude product were obtained. After column chromatography over silica gel (mobile phase 1:1 cyclohexane/ethyl acetate), 4.0 g of pure imidazole derivative were obtained as an oil.

$C_{17}H_{17}ClN_2$ (284.80) Calculated C 71.70 H 6.02 N 9.84 Found C 71.7 H 5.9 N. 9.6

EXAMPLE 2

(Compound 2)

1-Imidazolyl-(2-chloro-6-fluorophenyl)-1-cyclohexenylmethane.

3.3 g (10.7 mmol) of 1-imidazolyl-(2-chloro-6-fluorophenyl)-1-(1-hydroxycyclohexyl)-methane were dissolved in 19.5 ml of glacial acetic acid, 4.9 ml of concentrated sulfuric acid were then added and the mixture was heated at 100° C. for 1 hour and allowed to cool to room temperature. Working up was carried out analogously to Example 1. 2.9 g of imidazole derivative were isolated from 3.1 g of crude product by column chromatography (2:1 cyclohexane:ethyl acetate).

$C_{16}H_{16}ClFN_2$ (290.78) Calculated C 66.09 H 5.55 N 9.34 Found C 65.4 H 5.6 N 9.3

EXAMPLE 3

(Compound 3)

1-(1,2,4-Triazolyl)-2-chlorophenyl-(2-adamantylidene)methane.

7.0 g (10.4 mmol) of 1-(1,2,4-triazolyl)-2-chlorophenyl-2-(2-hydroxyadamantyl)-methane in a mixture of 36 ml of glacial acetic acid and 9 ml of concentrated $H_2SO_4$ were heated to 100° and stirred at this temperature for 2 hours. After the reaction mixture had cooled, it was worked up as in Example 1. 5.0 g of pure triazole derivative were obtained from 5.8 g of crude product by recrystallization from 1:1 hexane/isopropanol.

$C_{19}H_{20}ClN_3$ (325.85) Calculated C 70.04 H 6.19 N 12.89 Found C 69.9 H 6.3 N 12.5

The following compounds of the formula I were prepared analogously to Examples 1–3.

| EXAMPLE NO. | X, Y (phenyl substituents) | DOUBLE BOND EXOCYCLIC OR ENDOCYCLIC | R | Z | A | Mp. [°C.] |
|---|---|---|---|---|---|---|
| 4 | Cl (on phenyl) | endo | H | CH | $-(CH_2)_3-$ | Oil |

-continued
| EXAMPLE NO. | 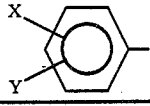 X/Y phenyl | DOUBLE BOND EXOCYCLIC OR ENDOCYCLIC | R | Z | A | Mp. [°C.] |
|---|---|---|---|---|---|---|
| 5 | 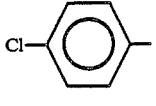 4-Cl | endo | H | CH | —(CH$_2$)$_4$— | Oil |
| 6 | 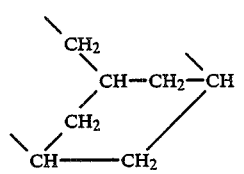 4-Cl | exo | —CH$_2$— | CH | 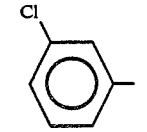 | 103 |
| 7 | 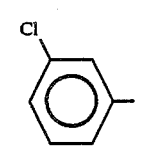 3-Cl | endo | H | CH | —(CH$_2$)$_4$— | Oil |
| 8 | 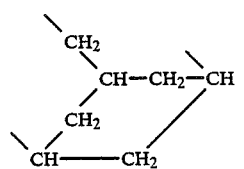 3-Cl | exo | —CH$_2$— | CH | 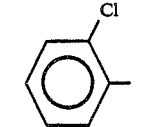 | 108 |
| 9 | 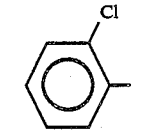 2-Cl | endo | H | CH | —(CH$_2$)$_5$— | Oil |
| 10 | 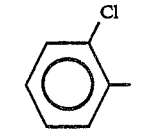 2-Cl | endo | H | CH |  —CH$_2$—CH(—C(CH$_3$)$_3$)—CH$_2$—CH$_2$— | Oil |
| 11 | 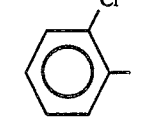 2-Cl | endo | H | CH | —CH$_2$—CH(C$_6$H$_5$)—CH$_2$—CH$_2$— | Oil |
| 12 | 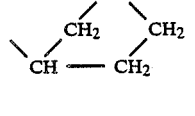 2-Cl | exo | H | CH | 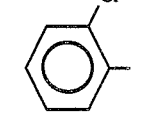 | Oil |
| 13 | 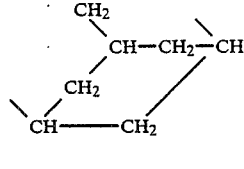 2-Cl | exo | —CH$_2$— | CH | (bicyclic CH$_2$ bridge) | 125 |

-continued

| EXAMPLE NO. | X,Y ring | DOUBLE BOND EXOCYCLIC OR ENDOCYCLIC | R | Z | A | Mp. [°C.] |
|---|---|---|---|---|---|---|
| 14 | 4-F phenyl | exo | —CH$_2$— | CH | bicyclic (norbornyl-type) | 117 |
| 15 | 2,4-Cl$_2$ phenyl | endo | H | CH | —(CH$_2$)$_4$— | Oil |
| 16 | 2,4-Cl$_2$ phenyl | endo | H | CH | —(CH$_2$)$_5$— | Oil |
| 17 | 2,4-Cl$_2$ phenyl | endo | H | CH | —(CH$_2$)$_{10}$— | 133 |
| 18 | 2,4-Cl$_2$ phenyl | exo | H | CH | cyclopentyl-type ring | Oil |
| 19 | 2,4-Cl$_2$ phenyl | exo | H | CH | bicyclic ring | Oil |
| 20 | 2,4-Cl$_2$ phenyl | exo | —CH$_2$— | CH | bicyclic (norbornyl-type) | 148 |
| 21 | 2,4-Cl$_2$ phenyl | endo | H | CH | —(CH$_2$)$_4$— | Oil |
| 22 | 2,6-Cl$_2$ phenyl | exo | —CH$_2$— | CH | bicyclic (norbornyl-type) | 114 |

-continued
| EXAMPLE NO. | 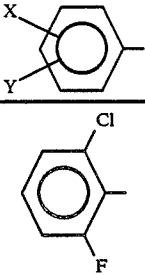 | DOUBLE BOND EXOCYCLIC OR ENDOCYCLIC | R | Z | A | Mp. [°C.] |
|---|---|---|---|---|---|---|
| 23 | 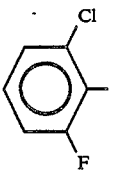 | endo | H | CH | —(CH$_2$)$_4$— | Oil |
| 24 | 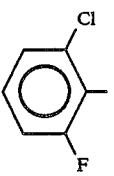 | endo | H | CH | —(CH$_2$)$_5$— | 78 |
| 25 | 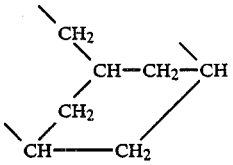 | exo | —CH$_2$— | CH | 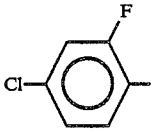 | 120 |
| 26 | 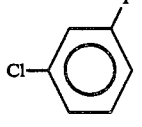 | endo | H | CH | —(CH$_2$)$_4$— | Oil |
| 27 | 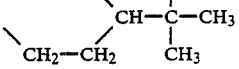 | endo | H | CH | 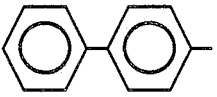 | Oil |
| 28 | 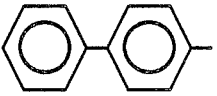 | endo | H | CH | —(CH$_2$)$_3$— | Oil |
| 29 | 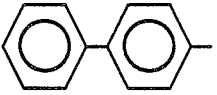 | endo | H | CH | —(CH$_2$)$_4$— | Oil |
| 30 | 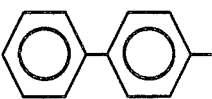 | endo | H | CH | —(CH$_2$)$_5$— | Oil |
| 31 | 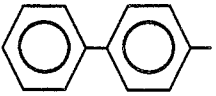 | endo | H | CH | —(CH$_2$)$_{10}$— | 97 |
| 32 | 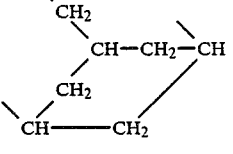 | exo | CH$_2$ | CH | | 177 |

-continued

| Example No. | X,Y-phenyl structure | Double bond exocyclic or endocyclic | R | Z | A | Mp. [°C.] |
|---|---|---|---|---|---|---|
| 33 | biphenyl (Z-Isomer) | exo | H | CH | –CH–CH₂–CH–CH–CH₂–CH₂–CH–CH₂ (bicyclic) | Oil |
| 34 | biphenyl (E-Isomer) | exo | H | CH | –CH–CH₂–CH–CH–CH₂–CH₂–CH–CH₂ (bicyclic) | 142° |
| 35 | biphenyl |  | H | N | —(CH₂)₄— | Oil |
| 36 | biphenyl |  | CH₃ | N | —(CH₂)₄— | Oil |

(A) Preparation of the starting material for compound 2

1-imidazolyl-(2-chloro,6-fluorophenyl)-1-(1-hydroxycyclohexyl)-methane.

10.6 g (50 mmol) of (2-chloro-6-fluorobenzyl)-1-imidazole were dissolved in 100 ml of tetrahydrofuran, and 32 ml (50 mmol) of n-butyllithium in hexane were added under a nitrogen atmosphere at −70° C. The mixture was stirred for a further half hour and 4.9 g (50 mmol) of cyclohexanone were then added at such a rate that the temperature could be kept at −70° C. The reaction mixture was warmed up to room temperature in the course of three hours, water was then added and the mixture was extracted with methylene chloride. Drying and concentrating the organic phase gave 14.8 g of crude carbinol, which was recrystallized from xylene. 11.6 g of white crystals of melting point 170° C. were obtained.

$C_{16}H_{18}ClFN_2O$ (308.78) Calculated C 62.44 H 5.57 N 9.1 Found C 62.8 H 5.9 N 9.2

(B) Preparation of the starting material for compound 3

1-(1,2,4-triazolyl)-2-chlorophenyl-2-(2-hydroxyadamantanyl)-methane.

66 ml (100 mmol) of n-butyllithium in hexane were added dropwise under a nitrogen atmosphere and at −78° C., to a solution of 9.7 g (50 mmol) of 1-(2-chlorobenzyl)-1,2,4-triazole and 6 g (50 mmol) of N,N,N',N'-tetramethylethylenediamine in 100 ml of tetrahydrofuran, the mixture was stirred for a further half hour at this temperature and 7.5 g (50 mmol) of 2-adamantanone in tetrahydrofuran were then added at such a rate that the temperature did not exceed −70° C. The reaction mixture was kept at −78° C. for a further 2 hours and was then allowed to warm up to room temperature. Working up with water/methylene chloride gave 17.4 g of crude product, which, after recrystallization from ethyl acetate, afforded 10.0 g of triazole derivative of melting point 178° C.

$C_{19}H_{22}ClN_3O$ (343.86) Calculated C 66.37 H 6.45 N 12.22 Found C 66.8 H 6.6 N 11.8

(C) Preparation of the starting material for compound 1

1-imidazolyl-4-chlorophenyl-2-(2-hydroxybicyclo[2.2.1]heptyl)-methane.

5.5 g (50 mmol) of 2-norbornane in 20 ml of tetrahydrofuran were slowly added dropwise at −70° C. to a solution, prepared analogously to Example 3, of 9.65 g (50 mmol) of 1-imidazolyl-4-chlorophenylmethyllithium in 100 ml of tetrahydrofuran, and the mixture was allowed to warm up to room temperature. Working up with water/methylene chloride gave 9.4 g of an oil, which, after recrystallization in 1:10 cyclohexane/ethyl acetate, afforded 8.1 g of crystals of melting point 118° C.

$C_{17}H_{19}ClN_2O$ Calculated C 67.44 H 6.32 N 8.74 Found C 67.9 H 6.6 N 8.5

We claim:

1. A compound of the formula Ia/Ib

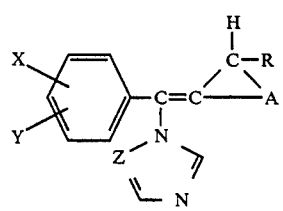

-continued

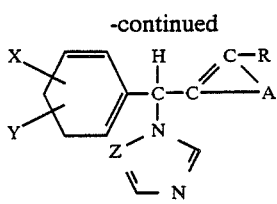

Ib in which
X and Y are identical or different and represent H, ($C_1$-$C_4$)-alkyl, phenyl, F, Cl, Br, ($C_1$-$C_4$)-alkoxy or ($C_1$-$C_4$)-alkylthio,
Z represents CH or N,
R represents H or ($C_1$-$C_4$)-alkyl or, if A is a bridged ($CH_2$)$_m$ chain having m=4 and 3 bridge carbon atoms, represents a methylene group attached to the middle bridge carbon atom,
A is a ($CH_2$)$_n$ chain in which n=1–10 and which can be unsubstituted or substituted by ($C_1$-$C_4$)-alkyl and phenyl, or A represents a bridged ($CH_2$)$_m$ chain having m=3 or 4 and 1–5 bridge carbon atoms, and physiologically acceptable salts with acids and stereoisomers thereof.

2. A compound of the formula Ia/Ib as claimed in claim 1, wherein at least one of the characteristics:
X and Y represents hydrogen, fluorine, chlorine or phenyl,
R repesents hydrogen or $CH_2$ and
A represents a ($CH_2$)$_n$ chain in which n=3–5 or a bridged ($CH_2$)$_m$ chain having m=3 or 4 and 1–5 bridge carbon atoms, is fulfilled.

3. A method of treating mycoses comprising the application to a host of an effective amount of a compound of formula Ia/Ib as claimed in claim 1.

4. A method for the prophylaxis and treatment of fungal infections which comprises administering to a host an effective amount of a compound of formula Ia/Ib as claimed in claim 1.

* * * * *